(12) United States Patent
Takagi et al.

(10) Patent No.: US 8,236,528 B2
(45) Date of Patent: *Aug. 7, 2012

(54) METHOD FOR METHANOL INDEPENDENT INDUCTION FROM METHANOL INDUCIBLE PROMOTERS IN *PICHIA*

(75) Inventors: Shinobu Takagi, Chiba (JP); Noriko Tsutsumi, Chiba (JP); Yuji Terui, Kanagawa (JP); XiangYu Kong, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/396,925

(22) Filed: Feb. 15, 2012

(65) Prior Publication Data

US 2012/0142053 A1 Jun. 7, 2012

Related U.S. Application Data

(62) Division of application No. 12/521,856, filed as application No. PCT/EP2008/050870 on Jan. 25, 2008, now Pat. No. 8,143,023.

(60) Provisional application No. 60/887,029, filed on Jan. 29, 2007.

(30) Foreign Application Priority Data

Jan. 26, 2007 (DK) .................................. 2007 00122

(51) Int. Cl.
*C12P 21/06* (2006.01)

(52) U.S. Cl. ...................................................... 435/69.1
(58) Field of Classification Search .................... None
See application file for complete search history.

(56) References Cited

FOREIGN PATENT DOCUMENTS

| EP | 0299108 B1 | 1/1989 |
|---|---|---|
| EP | 0340986 A2 | 11/1989 |
| EP | 0911416 B1 | 4/1999 |
| WO | 9003431 A1 | 4/1990 |
| WO | 0056903 A2 | 9/2000 |
| WO | 03014363 A1 | 2/2003 |
| WO | 03095653 A1 | 11/2003 |

OTHER PUBLICATIONS

Database—the promotor database of *Saccharomyces cerevisiae* Mar. 25, 2011.
Hartner et al, 2006, MicroCell Fac 5(39), 1-21.
Lin-Cereghino et al, 2006, Mol Cell Biol 26(3), 883-897.
Nakano et al, 2006, J Biosci Bioeng 101(3), 227-231.
Raschke et al, 1996, Gene 177(1), 163-167.

*Primary Examiner* — Suzanne M Noakes
*Assistant Examiner* — Jae W Lee
(74) *Attorney, Agent, or Firm* — Michael W. Krenicky

(57) ABSTRACT

A method for producing a polypeptide in a methylotrophic yeast host cell is described, where expression of the polypeptide is controlled by a methanol inducible promoter, including: i) expression of a positive regulator from a non-native promoter, the positive regulator activating transcription from the methanol inducible promoter, and ii) no addition of methanol.

17 Claims, No Drawings

METHOD FOR METHANOL INDEPENDENT INDUCTION FROM METHANOL INDUCIBLE PROMOTERS IN *PICHIA*

CROSS-REFERENCE TO RELATED APPLICATIONS

This application is a divisional application of U.S. application Ser. No. 12/521,856 filed Jun. 30, 2009 (now U.S. Pat. No. 8,143,023) which is a 35 U.S.C. 371 national application of PCT/EP2008/050870 filed Jan. 25, 2008, which claims priority or the benefit under 35 U.S.C. 119 of Danish application no. 2007 00122 filed Jan. 26, 2007 and U.S. provisional application No. 60/887,029 filed Jan. 29, 2007, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a method for producing a polypeptide in a methylotrophic yeast host cell, wherein expression of the polypeptide is controlled by a methanol inducible promoter.

BACKGROUND OF THE INVENTION

Eukaryotic organisms are widely used in industry as host cells for producing polypeptide for, e.g., pharmaceutical and industrial applications. The ability to manipulate gene transcription and expression gives the basis for providing higher production yields.

Conventionally, maximal expression of a gene in a eukaryotic organism is achieved by amplifying in the chromosome an expression cassette containing a single promoter operably linked to a gene encoding the polypeptide of interest and an amplifier selective marker.

Controlled expression is often desirable. In methylotrophic yeast it has been known for long that certain promoters are dependent on the presence of methanol in the growth medium for the induction of transcription. This induction by methanol requires the presence of additional factors, however, the exact mechanism of action for such factors have not been elucidated. Examples of positive factors known from yeast include Mxr1 p, described as a key positive regulator required for methanol utilization in *Pichia pastoris* (Lin-Cereghino et al., 2006, Mol Cell Biol 26(3): 883-897).

Examples of these methanol dependent promoters have been described in several yeast cells belonging to the group of yeast known as methylotrophic yeast. The promoters controlling expression of the enzymes involved in methanol metabolism in these organisms are particularly strong, and these promoters are generally used to control the heterologous expression of proteins in yeast. However, the specific carbon source used for the cultivation of these host cells has an enormous influence on the regulation of methanol metabolism promoters. Methanol and glycerol are considered as adequate substrates for methylotrophic yeast expression systems, while glucose has been considered inadequate (EP 299108). It is therefore desirable if expression from the known methanol metabolism promoters can be made less dependent on the substrate.

SUMMARY OF THE INVENTION

The invention provides a method for producing a polypeptide in a methylotrophic yeast host cell, wherein expression of the polypeptide is controlled by a methanol inducible promoter, comprising: i) expression of a positive regulator from a non-native promoter, said positive regulator activating transcription from the methanol inducible promoter, and ii) no addition of methanol. The invention further discloses a method for increasing the expression level of a heterologous polypeptide under the control of a methanol inducible promoter, comprising providing constitutive expression of the prm1 gene.

DETAILED DESCRIPTION OF THE INVENTION

The present invention relates to the controlled expression of polypeptides from methanol inducible promoters. Examples of these promoters have been described in several yeast cells belonging to the group of yeast known as methylotrophic yeast. In the context of the present invention a methylotrophic yeast is defined as a group of yeast which can utilize methanol as a sole carbon source for their growth. The promoters for the enzymes involved in methanol metabolism in these organisms are particularly strong, and these promoters (methanol metabolism promoters) are generally used to control the heterologous expression of proteins in yeast.

Known members of methylotrophic yeast host cells belong to the genera selected from the group consisting of *Pichia, Hansenula, Candida, Torulopsis*. According to the invention the *Pichia* host cell can in one embodiment be selected from the group consisting of P. *P pastoris, P. methanolica, P. angusta, P. thermomethanolica*. The *Hansenula* or *Candida* host cells can be selected from the group consisting of *H. polymorpha*, and *C. boidinii*.

Several promoters have previously been isolated and described in the literature from which the expression of heterologous polypeptides can be controlled by the addition of methanol to the growth medium. Such promoters include but are not limited to e.g. the AOX1 promoter (Alcohol Oxidase promoter), DHAS promoter (or DAS promoter) (dihydroxyacetone synthase promoter), FDH promoter (or FMDH promoter) (formate dehydrogenase promoter), MOX promoter (Methanol Oxidase promoter), AOX2 promoter, ZZA1, PEX5-, PEX8-, PEX14-promoter. Particularly the promoters useful in the present invention are promoters for enzymes involved in the methanol metabolism. Such promoters may be isolated from yeasts by the skilled person using conventional techniques. All of the above mentioned promoters have already been isolated from particular members of the group of methylotrophic yeast and by homology searches corresponding promoters from other members can easily be identified. This is further illustrated by the examples included herein. More particularly the promoters are selected from the group consisting of the formate dehydrogenase (FMD or FMDH) promoter, the methanol oxidase (MOX) promoters, the dihydroxyacetone synthase (DAS or DHAS) promoter or the alcohol oxidase (AOX1) promoter.

Normally all of the above promoters require the presence of methanol for their induction. This induction by methanol requires the presence of additional factors (such as transcription factors), however, the exact mechanism of action for such factors have not been elucidated. In yeast e.g. Mxr1p, has been described as a key positive regulator required for methanol utilization in *Pichia pastoris* (Lin-Cereghino et al., 2006, Mol Cell Biol 26(3): 883-897).

The inventors of the present invention have discovered that the controlled expression of a single positive factor, encoded by the Prm1 gene from *Pichia pastoris*, as described herein, can be sufficient in order to induce transcription from several methanol inducible promoters without the need for methanol in the growth medium. As disclosed herein this principle has been demonstrated using the Prm1 protein as a model protein for the positive activator and using the AOX1 or the DAS promoters for the controlled expression of a reporter polypeptide. The results obtained have shown that it is possible to induce the AOX1 or the DAS promoters simply by controlling the expression of the prm1 gene and without the presence of methanol in the growth medium.

In one embodiment of the invention the positive regulator is expressed constitutively from a suitable promoter. Preferably the promoter is not the native promoter meaning that the promoter controlling the expression of the positive regulator is different from the promoter normally controlling the expression. In the context of the present invention such preferred promoters are termed "non-native". The promoter could still be native to the host organism but it will be foreign in the context of the gene in question, e.g. the prm1 gene. In one particular embodiment the promoter is selected from the group consisting of the GAP promoter (glyceraldehyde-3-phosphate dehydrogenase promoter), the TEF1 promoter (Translational elongation factor EF-1 alpha promoter), and the PGK promoter (phosphoglycerate kinase promoter). The host cell according to the invention would normally express the positive regulator from an endogenous gene present on the chromosome in addition to the expression controlled by the non-native promoter as described above. In a further embodiment the endogenous copy of the gene encoding the positive regulator could be inactivated, e.g. by deletion, or the normal promoter controlling the endogenous copy of the gene could be replaced by the chosen non-native promoter.

In another embodiment the expression of the positive regulator is controlled from an inducible promoter which is not methanol inducible.

The positive regulator according to the invention is in one embodiment Prm1 as described herein. In one particular embodiment Prm1 comprises the amino acid sequence of SEQ ID NO: 1 or an allelic variant thereof; or a fragment thereof that has regulator activity.

In another particular embodiment, Prm1 consists of the amino acid sequence of SEQ ID NO: 1 or an allelic variant thereof; or a fragment thereof; or a substitution, deletion or addition of one or several amino acids that has regulator activity.

The term "polypeptide fragment" is defined herein as a polypeptide having one or more amino acids deleted from the amino and/or carboxyl terminus of SEQ ID NO: 1 or a homologous sequence thereof, wherein the fragment has regulator activity.

The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The relatedness between two amino acid sequences such as e.g. between two functional homologues is described by the parameter "identity".

For purposes of the present invention, the alignment of two amino acid sequences is determined by using the Needle program from the EMBOSS package version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; e.g. amino acids 1 to 989 of SEQ ID NO: 1 and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "|"). The length of a sequence is the number of amino acid residues in the sequence.

In the purely hypothetical alignment example below, the overlap is the amino acid sequence "HTWGER-NL" (SEQ ID NO:50) of Sequence 1; or the amino acid sequence "HGWGEDANL" (SEQ ID NO:51) of Sequence 2. In the example a gap is indicated by a "-".

Hypothetical Alignment Example:
Sequence 1: ACMSHTWGER-NL (SEQ ID NO:48)

|||||||

Sequence 2: HGWGEDANLAMNPS (SEQ ID NO:49)

In one embodiment according to the invention the functional homologue of Prm1 is at least 70% identical to SEQ ID NO: 1, particularly at least 80% identical to SEQ ID NO: 1, particularly at least 85% identical to SEQ ID NO: 1, particularly at least 90%, more particularly at least 95%, most particularly at least 98% identical to SEQ ID NO: 1.

In another embodiment the functional homologue of Prm1 is encoded by a polynucleotide which hybridizes under at least low stringency conditions with (i) nucleotides 1 to 2970 of SEQ ID NO: 2, or (ii) a complementary strand of (i).

In another embodiment the functional homologue of Prm1 is encoded by a polynucleotide which hybridizes under at least medium stringency conditions with (i) nucleotides 1 to 2970 of SEQ ID NO: 2, or (ii) a complementary strand of (i).

In another embodiment the functional homologue of Prm1 is encoded by a polynucleotide which hybridizes under at least high stringency conditions with (i) nucleotides 1 to 2970 of SEQ ID NO: 2, or (ii) a complementary strand of (i).

In another embodiment the functional homologue of Prm1 is encoded by a polynucleotide which hybridizes under very high stringency conditions with (i) nucleotides 1 to 2970 of SEQ ID NO: 2, or (ii) a complementary strand of (i).

The positive regulator according to the invention may also be a functional homologue of Prm1 isolated from other yeast cells. Such functional homologues can be isolated starting from the sequence shown in SEQ ID NO: 2, e.g. by using SEQ ID NO: 2 or a fragment thereof, to design a nucleic acid probe to identify and clone DNA encoding polypeptides having regulator activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labelled for detecting the corresponding gene (for example, with $^{32}$P, $^{3}$H, $^{35}$S, biotin, or avidin).

A genomic DNA or cDNA library prepared from such other organisms may, therefore, be screened for DNA which hybridizes with the probes described above and which encodes a polypeptide having regulator activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 2 or a subsequence thereof, the carrier material is used in a Southern blot.

For purposes of the present invention, hybridization indicates that the nucleotide sequence hybridizes to a labelled nucleic acid probe corresponding to the nucleotide sequence shown in SEQ ID NO: 2, its complementary strand, or a subsequence thereof, under very low to very high stringency conditions. Molecules to which the nucleic acid probe hybridizes under these conditions can be detected using X-ray film.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In a particular embodiment, the wash is conducted using 0.2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

As described above the positive regulator according to the invention may also be a functional homologue of Prm1 isolated from other yeast cells. According to one embodiment of the invention one such candidate could be Mut3 encoded by the mut3 gene from *Hansenula polymorpha* (syn. *Pichia angusta*). In the examples provided herein Prm1 has been overproduced in *Pichia pastoris*. It is however possible that the same effect can be obtained by overproducing Mut3 in *Pichia* or Prm1 in *Hansenula* or Mut3 in *Hansenula*. This has not been tested.

Therefore in a further embodiment of the invention the positive regulator is Mut3.

An increase in the level of positive regulator present in the host cell can also be provided by simply having multiple copies of the gene encoding the regulator present in the host cell.

Even though the exact mechanism of action of the positive regulator, Prm1, has not been elucidated it is most likely that the regulator will bind to the promoter region of the methanol inducible promoter. In one particular embodiment of the invention the methanol inducible promoter controlling the expression of a heterologous polypeptide is therefore provided with additional binding sites for the positive regulator thereby increasing the positive effect of the regulator.

The positive effect provided by increasing the level of positive regulator in the cell could be dependent on the presence other factors or it could be independent. One such other factor could be the Mxr1 protein (Lin-Cereghino et al., 2006, Mol Cell Biol 26(3): 883-897). Therefore in a further embodiment according to the invention expression of the mxr1 gene is also controlled by a non-native promoter, particularly the promoter selected from the group consisting of the GAP promoter, TEF1 promoter, and PGK promoter.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides produced by the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

In one particular embodiment the polypeptide produced from the host cell is heterologous to the host cell. In another embodiment the polypeptide is homologous to the host cell.

The effects observed in the present invention are illustrated in the examples below showing that expression from selected promoters can be observed without the addition of methanol to the growth medium. Addition of methanol could possibly further enhance the observed effect of increasing the level of Prm1 in the host cell. A further embodiment of the invention is therefore a method as described in all embodiments above for increasing the expression level of a heterologous polypeptide under the control of a methanol inducible promoter in which method methanol is present in the medium, and Prm1 is expressed at increased levels compared to a wild type cell. Preferably expression of the prm1 gene is constitutive.

EXAMPLES

Materials and Methods

Strains and Plasmids

*Pichia pastoris* GS115 (genotype:his4, Invitrogen™) was used as the host strain for protein expression. *E. coli* DH5alpha (Invitrogen™), TOP10 (Invitrogen™) or XL10 (Stratagene™) were used as cloning hosts in construction of the expression vectors. The plasmids pPIC9K and pGAPZα (Invitrogen™) were used for the construction of expression plasmids and pCR2.1-TOPO (Invitrogen™), pT7Blue (Novagen™) were used for sub-cloning of PCR fragments.

Transformation of *Pichia pastoris*:

*Pichia pastoris* strains are transformed by electroporation according to the manufacturer's protocol (Invitrogen, Cat. #K1710-01). Competent cells are prepared as described and stored in 40 μl aliquots at −70° C. Linearized plasmid DNA (500 ng) is mixed with 40 μl of competent cells and stored on ice for 5 min. Cells are transferred to an ice-cold 0.2 cm electroporation cuvette. Transformation is performed using a BioRad™ GenePulser II. Parameters used were 1500V, 25 μF and 200Ω. Immediately after pulsing, cells are suspended in 1 ml of ice cold 1 M sorbitol. The mixtures are plated on the relevant selection plates.

Medium and Assay

RD medium (1M sorbitol, 2% dextrose, 1.34% yeast nitrogen base, $4 \times 10^{-5}$% biotin, 0.005% L-glutamic acid, L-methinonine, L-lysine, L-leucine, and L-isoleucine, 2% agar noble) was used for the regeneration of transformants from *Pichia pastoris* GS115 with his4 selection. In case of the selection with zeocin resistance, YPD agar (1% yeast extract, 2% peptone, 2% glucose, 2% bacto agar) supplemented with 1M sorbitol and 100 micro g/mL zeocin was used for the regeneration. YPD (1% yeast extract, 2% peptone and 2% glucose), YPGly (1% yeast extract, 2% peptone and 2% glycerol) were used for the protein expression with *Pichia pastoris*. When necessary, methanol was added to the culture broth after 1 day and 2 days cultivation at the final concentration 1% or 2% (v/v). *E. coli* strains were cultivated with LB medium (1.0% tryptone, 0.5% yeast extract, 1.0% NaCl) with relevant antibiotics.

Phytase Assay Method:

7.5 mM of sodium phytate dissolved in the acetate buffer pH 5.5 is mixed with ½ volume of enzyme sample solution in the same acetate buffer containing 0.01% Tween 20. After the incubation at 37° C. for 30 minutes, the stop reagent containing 20 mM ammonium heptamolybdate and 0.06% ammonium vanadate dissolved in 10.8% nitric acid is added to generate yellow complex with released inorganic phosphate. The amount of released phosphate is measured photometrically as the absorbance at 405 nm. One phytase unit is defined as the amount of enzyme to release 1 μmol inorganic phosphate per minute.

Phytase Plate Assay:

20 μL of supernatant from the culture broth after 2-5 days incubation of the transformants is applied into a 4 mm hole punched in the following plate: 1% agarose plate containing 0.1 M Sodium acetate (pH 4.5) and 0.1% Inositol Hexaphosphoric acid. The plate is incubated at 37° C. over night and a buffer consisting of 1M $CaCl_2$ and 0.2M Sodium acetate (pH 4.5) is poured over the plate. The plate is left at room temperature for 1 h and the phytase activity identified as a clear zone.

PCR Conditions

PCR reaction was typically carried out in the following or equivalently conditions: Reaction mixtures contained 2 mM dNTP, 10 pmol of forward and reverse primer, 2.8 unit of Expand high fidelity mixture (Roche), 1× Expand high fidelity buffer (Roche), and 100 μg of template DNA. Reaction conditions are, for example;

| Temp (° C.) | Time | Cycle |
| --- | --- | --- |
| 95 | 5 min | 1 |
| 95 | 15 sec | 35 |
| 48 | 30 sec | |
| 68 | 3.5 min | |
| 68 | 10 min | 1 |

Example 1

Constitutive Expression of Prm1 in a Strain Expressing a Phytase Gene Under DAS1 Promoter Control Cloning of TEF1 Promoter and Construction of pNo-TP10

Cloning of TEF1 (Translation Elongation Factor1) promoter from *Pichia pastoris* was carried out by the following procedure. By alignment of the homologous regions of the TEF1 proteins from the yeasts *Saccharomyces cervisiae*, *Candida albicanse*, and *Hanseniaspora uvarum*, the following degenerated primes were designed.

TEF1(f); 5'-ttyaartaygcntgggt-3' (protein; FKYAWV) SEQ ID NO: 6 and 7

TEF5(r); 5'-arytgytcrtgrtgcatytc-3' (protein; EMHHEQL) SEQ ID NO: 8 and 9

PCR was carried out using 50 microL of reaction including 4 mM dNTP, 10 microM of each primer, 1 unit of Taq polymerase (Roche), 1× Taq buffer (Roche), and 100 ng of genomic DNA of GS115 DNA. The PCR conditions were as shown below.

| temp | time | cycle |
| --- | --- | --- |
| 94° C. | 1 min | 30 |
| 55° C. | 1 min | |
| 72° C. | 3 min | |

The amplified 0.7 kbp fragment was purified and subcloned into TA-cloning vector, pTBlue7. The resulting plasmid was used for the sequence determination. The obtained DNA sequence and presumed amino acid sequence are shown in SEQ ID NO: 3 and SEQ ID NO: 4 respectively. Since the obtained sequences had similarity to known TEF1 proteins, cloning of the upstream region (SEQ ID NO: 5) comprising the promoter sequence was carried out using DNA walking Speed Up premix kit (Seegene, K1501) together with the following specific primers.
TEF-TSP1; 5'-tgacggtaacgtggtactt-3' SEQ ID NO: 10
TEF-TSP2; 5'-ggagtctcgaacttccacaa-3' SEQ ID NO: 11
TEF-TSP3; 5'-agcgatgtcgatggtgatac-3' SEQ ID NO: 12

PCR was carried out using the 50 microL of reaction mixture including 4 mM dNTP, 10 microM of TEF-TSP1 primer, 2.5 microM of DW-ACP2 primer in the kit, 1 unit of Taq polymerase (Roche), 1× Taq-buffer (Roche), and 100 ng of genomic DNA. The PCR program was as shown below.

| temp | time | cycle |
|---|---|---|
| 94° C. | 5 min | 1 |
| 42° C. | 1 min | |
| 72° C. | 2 min | |
| 94° C. | 30 sec | 20 |
| 55° C. | 30 sec | |
| 72° C. | 100 sec | |
| 72° C. | 7 min | 1 |

A second PCR was carried out using 20 microL of reaction mixture including 2 mM dNTP, 10 microM of TEF-TSP2 primer, 10 microM of DW-ACPN primer from the kit, 0.4 units of Taq polymerase (Roche), 1× Taq-buffer (Roche), and 5 micro L of the purified PCR product from the first round with the following program:

| temp | time | cycle |
|---|---|---|
| 94° C. | 3 min | 1 |
| 94° C. | 30 sec | 30 |
| 58° C. | 30 sec | |
| 72° C. | 100 sec | |
| 72° C. | 7 min | 1 |

A third PCR was carried out using 50 microL of reaction including 2 mM dNTP, 10 microM of TEF-TSP3 primer, 10 microM of Universal primer from the kit, 1 unit of Taq polymerase (Roche), 1× Taq-buffer (Roche), and 1 micro L of 10 times diluted PCR product from the second round with the following program:

| temp | time | cycle |
|---|---|---|
| 94° C. | 3 min | 1 |
| 94° C. | 30 sec | 30 |
| 65° C. | 30 sec | |
| 72° C. | 100 sec | |
| 72° C. | 7 min | 1 |

After three times nested PCR, a 1.2 kbp fragment was amplified. This fragment was sub-cloned into pT7Blue and the sequence was determined. The obtained sequence is shown in SEQ ID NO: 5. The 1.2 kbp region upstream of TEF10RF was used as TEF1 promoter for further experiment.

The plasmid pNo-TP10 is an expression plasmid for bacterial phytase under TEF1 promoter and carries a zeocin resistant marker gene. Construction of pNo-TP10 was carried out as described. The TEF1 promoter and the codon optimized phytase gene was cloned from genomic DNA of *Pichia pastoris* A94 (see Example 2) using the following primers.

Primer 1 and 2 were used for the amplification of TEF1 promoter and primer3 and 4 were used for phytase gene.
primer1; 5'-tacagggcgcgtggggatatcggatccagctcatctaggga-3' (BamHI is underlined) (SEQ ID NO: 13)
primer2; 5'-tgaagatggatgggaatctcatatggt-tggcgaataactaaaatgtatgt-3' (SEQ ID NO: 14)
primer3; 5'-acatacattttagttattcgccaac-catatgagattcccatccatcttca-3' (SEQ ID NO: 15)
primer4; 5'-taattcgcggccgccctaggqaattct-tactcggtgacagcgcactcggg-3' (EcoRI is underlined) (SEQ ID NO: 16)

PCR was carried out using 50 microL reaction including 2 mM dNTP, 10 microM of each primer, 2.8 unit of Expand high fiderlity mixture (Roche), 1× Expand high fidelity buffer (Roche), and 100 ng of genomic DNA. The PCR program was as shown below.

| temp | time | cycle |
|---|---|---|
| 94° C. | 2 min | 1 |
| 94° C. | 10 sec | 11 |
| 50° C. | 30 sec | |
| 68° C. | 3 min | |
| 94° C. | 10 sec | 20 |
| 50° C. | 30 sec | |
| 68° C. | 3 min + 20 sec/cycle | |
| 68° C. | 7 min | 1 |

An amplified 1.2 kbp fragment of the TEF1 promoter and a 1.5 kbp fragment containing the phytase gene including secretion signal were purified using gel extraction and they were subjected to a second round of PCR with primer1 and primer4 in order to fuse these fragments using the overlap generated in the first PCR. PCR was carried out using the 50 microL of reaction including 2 mM dNTP, 10 microM of each primer, 2.8 unit of Expand high fiderlity (Roche), 1× Expand high fidelity buffer (Roche), and 1 µl of the purified TEF1 promoter and 1 µl of the purified phytase gene. The PCR program was as shown below.

| temp | time | cycle |
|---|---|---|
| 94° C. | 2 min | 1 |
| 94° C. | 10 sec | 11 |
| 58° C. | 30 sec | |
| 68° C. | 3 min | |
| 94° C. | 10 sec | 20 |
| 58° C. | 30 sec | |
| 68° C. | 3 min + 20 sec/cycle | |
| 68° C. | 7 min | 1 |

The amplified 2.7 kbp fragment was sub-cloned into pT7Blue and the resultant plasmid was designated pT12-8. The BamHI-EcoRI fragment from pT12-8 including the TEF1 promoter and the phytase gene was ligated with pGAPZα cut with BglII and EcoRI to result in pNo-TP10.

Cloning of DAS1 Promoter and Construction of pNo-DP3

The DAS1 promoter is known to be strongly inducible by methanol in *Candida boidinii* (Yurimoto, H. Komeda, T. Lim, C. R. Nakagawa, T. Kondo, K. Kato, N. Sakai, Y.; Biochim. Biophys. Acta 1493(1-2):56-63 (2000).) The DAS1 gene encoding dihydroxyacetone synthase was found in the genome sequence of *Pichia pastoris* by blast search as the homologue to the DAS1 gene of *Candida boindinii* (EMBL: AF086822). Around 1 kb of 5'-untranslated region of the DAS1 gene was isolated as a promoter region from genomic DNA of *Pichia pastoris* by PCR using the primers shown below;

primer43; 5'-ttttggtcatgcatgacgtcatagggagaaaaaccgagac-3' (NsiI site is underlined) (SEQ ID NO: 17)

primer44; 5'-ctcatatqttttgatgtttgatagtttga-3' (NdeI site is underlined) (SEQ ID NO: 18)

The amplified 1 kb fragment was sub-cloned into the NsiI/NdeI sites of pCR2.1-TOPO and used for the sequence determination of this fragment (SEQ ID NO: 19). The 1 kb of DAS1 promoter region was excised as an NsiI/NdeI fragment from pCR2.1-TOPO and ligated with pNo-TP10 digested with NsiI/NdeI generating pNo-DP2. To change the marker gene from zeocin resistant gene to His4 gene, a 1.4 kb AatII fragment containing the DAS1 promoter and a part of bacterial phytase gene from pNo-DP2 was ligated to a 9.0 kb of AatII fragment from pPICNoT-G01651 (See Example 2) containing the rest of phytase gene and the His4 gene and bacterial vector. The generated plasmid was named pNo-DP3.

Cloning of Prm1 and Construction of pGPrm

A gene, which we have named, Prm1 (positive regulator for methanol), and which encodes a novel positive regulator of methanol inducible promoters, was isolated from genomic DNA of *Pichia pastoris* by PCR using the primers shown below;

primer 32; 5'-actatttcgaaatgcctcctaaacatcggctg-3', (BstBI site is underlined) (SEQ ID NO: 20)

primer 33; 5'-gtcgacttaactgcaaaatttattg-3' (SalI is underlined) (SEQ ID NO: 21)

PCR was carried out using the 50 µL of reaction including 1×LA PCR buffer II (TAKARA), 2.5 U of LA taq (TAKARA), 2.5 mM MgCl$_2$, 2.5 mM dNTP, 1 microM of each primer, 100 ng of genomic DNA with the following program:

| temp   | time   | cycles |
|--------|--------|--------|
| 94° C. | 30 sec | 30     |
| 55° C. | 30 sec |        |
| 72° C. | 4 min  |        |

The obtained 1 kb of fragment was sub-cloned into pCR2.1-TOPO. After confirmation of the sequence, a 1 kbp fragment comprising the Prm1 gene (SEQ ID NO: 2) was cloned into pGAPZα (Invitrogen) using the BstBI and SalI restriction sites, resulting in pGPrm. The plasmid pGPrm carries the Prm1 gene under GAP promoter control and a zeocin resistance gene as the selection marker.

Constitutive Expression of Prm1 in DAS40, a Strain Expressing Phytase Under DAS1 Promoter The plasmid pNo-DP3 was transformed into *Pichia pastoris* GS115 with his4 selection. The generated transformants were re-isolated and tested for phytase expression using YPD medium with methanol addition. One transformant, DAS40, was selected as the strain which showed phytase activity in presence of methanol.

The plasmid pGPrm was transformed into the *Pichia pastoris* DAS40, and transformants were isolated on zeocin plates. Generated transformants were cultivated in YPD medium at 30° C. for 2 days with agitation, and phytase activity in the supernatant of the culture broth was measured by phytase assay. The results are shown in the table below.

| Strain        | Relative phytase activity |
|---------------|---------------------------|
| Transformant A | 44.2                     |
| Transformant B | 13.3                     |
| Transformant C | 7.6                      |
| DAS40         | 1                         |

Example 2

Constitutive Expression of Prm1 in the Strain Expressing a Phytase Gene Under AOX1 Promoter Media:
MD (1.34% YNB, 4×10$^{-5}$% biotin, 2% dextrose)
BMSY (1% yeast extract, 2% peptone, 100 mM potassium phosphate buffer, pH 6.0, 1.34% YNB, 4×10$^{-5}$% biotin, 1% sorbitol)

Vector:
pPIC-NoT, *Pichia pastoris* expression vector under AOX1 promoter, which was derived by eliminating the alpha-secretion signal from pPIC9K (Invitrogen™)

To create pPIC-NoT vector plasmid pPIC9K was digested with BamHI and EcoRI, and the digested major fragment was isolated from agarose gel. A synthetic DNA fragment containing BamHI and EcoRI sites were created by annealing the following two oligoes:
NoT-1 P-GATCCTACGTAGCTGAG (SEQ ID NO: 22) and
NoT-2 P-AATTCTCAGCTACGTAG (SEQ ID NO: 23)

The above synthetic DNA fragment was ligated into the digested pPIC9K plasmid, and the resulting vector pPIC-NoT was verified by sequencing.

PCR Primers:

| Oligo Name | Oligo Seq |
|------------|-----------|
| OA-Na | GATCCAAACCATGAGATTCCCATCCATCTTCACTG (SEQ ID NO: 24) |
| OA-Nb | CAAACCATGAGATTCCCATCCATCTTCACTG (SEQ ID NO: 25) |
| OAPhy-R | CATTCTGTTCCTCTCTCTTTTCCAAGGAAACACCTTC (SEQ ID NO: 26) |
| OAPhy-F | ggaaaagagaGAGGAACAGAATGGAATGAAGTTGG (SEQ ID NO: 27) |
| OPhy-Ca | AATTCTTACTCGGTGACAGCGCACTC (SEQ ID NO: 28) |
| OPhy-Cb | CTTACTCGGTGACAGCGCACTC (SEQ ID NO: 29) |

Plasmid:
pPICNoT-G01651

A codon optimized *Citrobacter braakii* phytase gene was used in pPICNoT-G01651 in order to increase the expression yield of the cb phytase in *Pichia pastoris*. The wild type *Citrobacter braakii* phytase gene was modified based on *P. pastoris*-preferred codon usage, by means of replacing rare codons, eliminating repetitive AT and decreasing the GC content. The designed sequence was also analyzed to avoid potential intron.

The modified phytase genes (G01651) fused to a modified alpha-factor secretion signal sequence were designed based on the codon bias of *P. pastoris*. The *P. pastoris* codon usage table is from www.kazusa.jp as well as Zhao et al, 2000 (Zhao X, Huo K K, Li Y Y. Synonymous condon usage in *Pichia pastoris*. Chinese Journal of Biotechnology, 2000, 16(3): 308-311). Rare codons for arginine were eliminated. Besides substitution of rare codons, the total G+C content was decreased below 50%, and AT-rich regions were modified to avoid premature termination. In addition, cryptic introns within modified coding regions were eliminated as described in co-pending Danish patent application PA 2006 01042/NZ10978.000-DK. The synthetic gene sequence is shown in SEQ ID NO: 30 (complete ORF without signal sequence).

The expression plasmid pPICNoT-G01651 was generated as described below:

The PCR fragment encoding the mature form of cb phytase (SEQ ID NO: 30) fused inframe with optimized α-factor signal peptide (SEQ ID NO: 31) was created by overlap extension PCR method as follows: the fragment I containing α-factor signal peptide was amplified from pJ2:G01468 plasmid (pJ2:G01468 was generated by DNA2.0, and contains the mature form of plectasin fused with α-factor secretion signal which was modified based on *P. pastoris* codon usage) with specific primers OA-Na and OAPhy-R, while the fragment II encoding mature phytase was amplified from plasmid pJ2:G01651 (generated by DNA2.0 and contains the synthetic phytase gene encoding mature form of C. braakii phytase) using specific primers OAPhy-F and OPhy-Ca. Then fragment I and II were mixed and used as a template for $2^{nd}$ step PCR amplification with specific primers OA-Na/b and OPhy-Ca/b to obtain the targeted PCR fragment. The DNA fragment was purified by gel extraction kit then subcloned into pPIC-NoT vector at BamHI and EcoRI sites. The resulting expression construct was confirmed by sequencing.

Expression Test in a 3 ml Scale:

Expression test of the selected transformants was done in a 3 ml scale using 24-deep well plates (Whatman, UK). Each transformant was grown in BMSY media for 2.5 days at 28° C. with vigorous shaking (200 rpm); then 300 μl 0.5% methanol was added to each well every day for 4 days to induce heterogeneous gene expression. Samples of medium culture were taken daily during induction, stored at −20° C. for phytase activity assay.

Constitutive Expression of Prm1 in A94, a Strain Expressing Phytase Under AOX1 Promoter The expression plasmid pPICNoT-G01651 was transformed into *Pichia pastoris* GS115 with his4 selection, and generated transformants on MD agar with 1M sorbitol were re-isolated and tested for phytase expression in 3 ml scale. One isolate, A94, was selected as the strain which shows phytase activity in presence of methanol. The plasmid pGPrm was subsequently transformed into A94 and transformants were isolated with zeocin resistance. Isolated transformants were cultivated in YPD medium at 30° C. for 2 days with agitation, and phytase activities in the culture supernatants were measured by phytase assay. The results are shown in the table below.

| Strain | Relative phytase activity |
|---|---|
| Transformant 1 | 1.86 |
| Transformant 2 | 2.57 |
| Transformant 3 | 3.0 |
| A94 | 1 |

Example 3

Gene Disruption of Prm1 in *Pichia pastoris* GS115 and Derived Strains

A 1571 bp gene fragment 5' to the PRM1 gene was amplified by PCR using the primers:
JP23/PRM1-5'-forw-NY: 5' GCGCGAATTCCACAGGGCTTGCTAAGAAATC 3' (SEQ ID NO: 32); and
JP26/PRM1-5'-rev-NY: 5' GAAGGGAGATTAATACAGGGC 3' (SEQ ID NO: 33)

A 1473 bp gene fragment 3' to the PRM1 gene was amplified by PCR using the primers:
JP17/PRM1-3'-forw-NY: 5' GATTGGACCACTGCGCCAGATAC 3' (SEQ ID NO: 34); and
JP19/PRM1-3'-rev-NY: 5' GCGCGTCGACCCACCCGAGGATAAGAAGG 3' (SEQ ID NO: 35)

A 3382 bp fragment containing the HIS4 gene including promoter and terminator was amplified by PCR using the primers below (in each end the fragment contains a 20 bp overlap to PRM1 5' and 3' regions, respectively, intended for SOE-PCR);
JP13/HIS4-forward-NY: 5' CCCTGTATTAATCTCCCTTCATCAGAATTGGTTAATTGGTTG 3' (SEQ ID NO: 36); and
JP15/HIS4-rev-NY: 5' TCTGGCGCAGTGGTCCAATCATCGATAAGCTTTAATGCGG 3' (SEQ ID NO: 37)

The three above described gene fragments are fused in the following order: PRM1-5'+HIS4+PRM1-3') using SOE-PCR (Splicing by Overlapping Extension PCR) creating a prm1 deletion fragment having the selectable HIS4 marker flanked by the 5' prm1 fragment and the 3' prm1 fragment.

The prm1 deletion fragment was subsequently transformed into GS115 (having a his-4-minus phenotype) which allows for selection of transformants on a minimal medium without histidine. A strain deleted for the prm1 gene, PFJo435, was characterized by PCR analysis. Three different PCR's were run in order to verify a correct prm1-deletion:

A) A PCR that would give a product of 704 bp in case PRM1 was NOT deleted—using primers:
JP58/PRM1-orf-forw-test7: 5' CTGGAGCAGAGTATACAGCC 3' (SEQ ID NO: 38); and
JP59/PRM1-orf-rev-test8: 5' CTCAATAAATGCGGGTCTGTG 3' (SEQ ID NO: 39)

B) A deletion specific PCR that would give a product of 1950 bp in case of PRM1 deletion—using primers:
JP31/PRM1-5'-forw-test1: 5' CCTGGTTGATCAGCTCCACC 3' (SEQ ID NO: 40); and
JP33/HIS4-rev-test3: 5' CCCGTCAAGTCAGCGTAATGC 3' (SEQ ID NO: 41)

C) A deletion specific PCR that would give a product of 1550 bp in case of PRM1 deletion—using primers:
JP32/PRM1-3'-rev-test2: 5' CTCCCTCTCCAGCTGCTTCG 3' (SEQ ID NO: 42); and
JP34/HIS4-forw-test4: 5' CGGTGCCTGACTGCGTTAGC 3' (SEQ ID NO: 43)

Strain PFJo435 did not result in a PCR product from PCR A, but resulted in the predicted deletion specific PCR product from B and C—showing that PRM1 has been deleted in PFJo435.

A Prm1 gene deletion mutant of GS115, PFJo435, could not grow on MM (1.34% YNB, $4 \times 10^{-5}$% biotin, 2% methanol), while a wild type strain, GS115H, showed nice growth after 2 days cultivation at 30° C. The expression levels from the AOX or DAS promoters in the presence of methanol, e.g. measured as the phytase gene expression under the control of the DAS promoter or AOX promoter in DAS40 or A94 derivatives, were reduced in the Prm1 deleted derivatives. The reduced activity is attributed, to some extent by the exogenous Prm1 gene. The results on the DAS promoter are shown below.

| Strain construction | phytase yield with methanol (relative) | phytase yield with glucose (relative) |
|---|---|---|
| PFJo435/pNo-DP2 (DAS-phytase) | 0.015 | 0.9 |
| PFJo435/pNori12 (DAS-phytase + GAP-Prm) | 0.43 | 3.7 |
| DAS 40 | 1 | 1 |

DAS40 and pNo-DP2 are described before in example 1.
Construction of pNori12 are shown below.
Construction of pNori12

For the co-expression of the phytase gene from the DAS promoter and the Prm 1 gene from the GAP promoter, pNori12 was constructed.

To replace the terminator part, the original terminator of Prm was cloned using following primers:
pr136; 5'-ataaattttgacagttaagtcgacctctgtaaattaattgataatttcaa-3' (SEQ ID NO: 44)
pr137; 5'-caatgatgatgatgatgatggtc-gacgtttaaacttaattaaaagggaaatttacaagcc-3' (SEQ ID NO: 45)

PCR was carried out using a total of 50 microL reaction mixture including 2 mM dNTP, 10 microM of each primer, 2.8 unit of Expand high fidelity plus (Rosche), 1× Expand high fidelity buffer (Rosche), and 100 ng of genomic DNA of GS115. The PCR program was as described below.

| temp | time | Cycle |
|---|---|---|
| 94° C. | 2 min | 1 |
| 94° C. | 10 sec | 11 |
| 55° C. | 30 sec | |
| 68° C. | 3 min | |
| 94° C. | 10 sec | 20 |
| 55° C. | 30 sec | |
| 68° C. | 3 min + 20 sec/cycle | |
| 68° C. | 7 min | 1 |

The amplified 500 bp of fragment was inserted in the SalI site of pGPrm using In-Fusion PCR cloning kit (Clontech) to fuse it with the ORF of Prm, resulting in pNori11. In order to make the expression plasmid which has GAP-Prm and DAS-phytase, the 3354 bp of SnaBI-XmaI fragment which carries a phytase expression cassette containing DAS promoter was isolated from pNo-DP2 and ligated to 5323 bp of XmaI-PmeI fragment of pNori11, resulting in pNori12. The plasmid pNori12 carries the Prm1 gene under GAP rpmoter control, phytase gene under DAS promoter control, and a zeocin resistant gene as the selection marker.

Example 4

Constitutive Expression of Mxr1

Mxr1, a gene from *Pichia pastoris* reported to be a positive regulator for methanol induction (G. P. Lin-Cereghino et al.; MOLECULAR AND CELLULAR BIOLOGY, February 2006, p. 883-897 Vol. 26, No. 3), was isolated from genomic DNA of *Pichia pastoris* by PCR using the primers Mxr-F and Mxr-R. The sequence of the primers and the PCR conditions are shown below.

PCR Primers:

| Oligo name | Oligo Seq |
|---|---|
| Mxr-F | ATTGAACAACTATTTCGAAACCATGAGCAATCTACCCCC (SEQ ID NO: 46) |
| Mxr-R | GAGTTTTTGTTCTAGAATGACACCACCATCTAGTCGG (SEQ ID NO: 47) |

PCR Conditions

| Temp (° C.) | Time | Cycles |
|---|---|---|
| 95 | 5 min | 1 |
| 95 | 15 sec | 35 |
| 48 | 30 sec | |
| 68 | 3.5 min | |
| 68 | 10 min | 1 |

A 3.5 kbp PCR fragment digested with BstBI and XbaI was mixed with pGAPZα digested with the same enzymes followed by ligation. The resulting plasmid pGMxr carries the Mxr1 gene under GAP promoter control and a zeocin resistance gene as the transformation marker. The plasmid pGMxr was transformed into *Pichia pastoris* DAS40 and/or A94. The transformants were isolated on zeocin plates. Generated transformants were cultivated in YPD medium at 30° C. for 2 days with agitation, and phytase activity in the supernatant of culture broth was measured. The effect of constitutive expression of the Mxr 1 gene was observed as increased phytase activity in YPD medium in the transformants after introduction of pGMxr.

| Transformant | pGMxr | phytase activity by plate assay |
|---|---|---|
| Mxr#23/DAS40 | Yes | + |
| DAS40 | No | − |

| Transformant | pGMxr | Phytase yield (relative) |
|---|---|---|
| AMxr2/A94 | Yes | 7.6 |
| A94 | No | 1 |

The plasmid pGMxr is modified to replace the selection marker gene with e.g. ura3, ade2, arg4, hygromycin resistant gene, resulting in pGMxr-m. Furthermore, the promoter region can be replaced with another promoter such as PGK1 promoter or TEF1 promoter, giving pPMxr-m or pTMxr-m. The plasmid pGMxr-m, pPMxr-m or pTMxr-m is transformed into *Pichia pastoris* Transformant A or Transformant 3 with necessary modification for the transformation. Newly generated transformants are cultivated in YPD medium at 30° C. for 2 days with agitation, and phytase activity in the supernatant of culture broth is measured.

The invention claimed is:

1. A method for producing a polypeptide in a methylotrophic yeast host cell, wherein expression of the polypeptide is controlled by a methanol inducible promoter, comprising: i) expression of a positive regulator from a non-native promoter, said positive regulator activating transcription from the methanol inducible promoter, and ii) no addition of methanol, and wherein said positive regulator Prm1 having at least 98% sequence identity to SEQ ID NO:1.

2. The method according to claim 1, wherein the methylotrophic yeast host cell is selected from the group consisting of *Pichia, Hansenula, Candida*, and *Torulopsis*.

3. The method according to claim 1, wherein the methanol inducible promoter is selected from the group consisting of the AOX1 promoter, DHAS promoter, FDH promoter, FMDH promoter, MOX promoter, AOX2 promoter, ZZA1, PEX5-, PEX8-, PEX14-promoter.

4. The method according to claim 1, wherein expression of the positive regulator is constitutive.

5. The method according to claim 1, wherein the positive regulator consists of the amino acid sequence of SEQ ID NO: 1.

6. The method according to claim 4, wherein the positive regulator is under the control of the GAP promoter, TEF1 promoter or PGK promoter.

7. The method according to claim 1, wherein expression of the positive regulator is inducible.

8. The method according to claim 1, comprising at least two genes encoding the positive regulator.

9. The method according to claim 1, wherein the methanol inducible promoter is provided with additional binding sites for the positive regulator.

10. The method according claim 2, wherein the *Pichia* host cell is selected from the group consisting of *Pichia pastoris, Pichia methanolica, Pichia angusta* and *Pichia thermomethanolica*.

11. The method according to claim 2, wherein the *Hansenula* host cell is selected from the group consisting of *Hansenula polymorpha*.

12. The method according to claim 2, wherein the *Candida* host cell is selected from the group consisting of *Candida boidinii*.

13. The method according to claim 1, wherein the promoter controlling the endogenous copy of the positive regulator is also replaced by a non-native constitutive promoter.

14. The method according to claim 1, wherein the polypeptide is heterologous to the host cell.

15. The method according to claim 1, wherein the polypeptide is homologous to the host cell.

16. The method of claim 1, wherein the positive regulator has at least 99% sequence identity to SEQ ID NO:1.

17. A method for increasing the expression level of a heterologous polypeptide under the control of a methanol inducible promoter, comprising providing a methylotrophic yeast cell having constitutive expression of the prm1 gene as set forth in SEQ ID NO:2 and expressing said heterologous polypeptide in the absence of methanol.

* * * * *

SEQUENCE LISTING

<160> NUMBER OF SEQ ID NOS: 51

<210> SEQ ID NO 1
<211> LENGTH: 989
<212> TYPE: PRT
<213> ORGANISM: Pichia pastoris

<400> SEQUENCE: 1

Met Pro Pro Lys His Arg Leu Glu Gln Ser Ile Gln Pro Met Ala Ser
1               5                   10                  15

Gln Gln Ile Val Pro Gly Asn Lys Val Ile Leu Pro Asn Pro Lys Val
            20                  25                  30

Asp Ala Lys Ser Thr Pro Asn Ile Ser Val Gln Lys Arg Arg Arg Val
        35                  40                  45

Thr Arg Ala Cys Asp Glu Cys Arg Lys Lys Val Lys Cys Asp Gly
    50                  55                  60

Gln Gln Pro Cys Ile His Cys Thr Val Tyr Ser Tyr Glu Cys Thr Tyr
65                  70                  75                  80

Ser Gln Pro Ser Ser Lys Lys Arg Gln Gly Gln Ser Leu Ser Leu Ser
                85                  90                  95

Ala Pro Ser Asn Ile Asn Ala Thr Ser Ser Val Gln Lys Ser Val Lys
            100                 105                 110

Pro Pro Glu Ile Asp Phe Gln Arg Met Arg Asp Ala Leu Lys Tyr Tyr
        115                 120                 125

Glu Asp Leu Leu Asn Gln Leu Ile Tyr Pro Asn Ser Ala Pro Thr Val
    130                 135                 140

Arg Val Asn Pro Ile Arg Leu Ala Ser Ile Leu Lys Gln Leu Arg Ala
145                 150                 155                 160

Asp Lys Ser Ser Asp Glu Leu Ile Ser Val Lys Ala Leu Ser Asp Asn
                165                 170                 175

Tyr Ile Glu Met Leu His Lys Thr Met Gln Gln Pro Val Gln Gln Pro
            180                 185                 190

Ala Pro Pro Ser Leu Gly Gln Gly Gly Ser Phe Ser Asn His Ser Pro
        195                 200                 205

Asn His Asn Asn Ala Ser Ile Asp Gly Ser Ile Glu Ser Asn Leu Gly
    210                 215                 220

Arg Glu Ile Arg Ile Ile Leu Pro Pro Arg Asp Ile Ala Leu Lys Leu
225                 230                 235                 240

Ile Tyr Lys Thr Trp Asp Asn Ala Cys Val Leu Phe Arg Phe Tyr His
                245                 250                 255

Arg Pro Ala Phe Ile Glu Asp Leu Asn Glu Leu Tyr Glu Thr Asp Leu
            260                 265                 270

Ala Asn Tyr Thr Asn Lys Gln Gln Arg Phe Leu Pro Leu Val Tyr Ser
        275                 280                 285

Val Met Ala Cys Gly Ala Leu Phe Cys Lys Thr Asp Gly Ile Asn His
    290                 295                 300

Gly Gln Lys Ser Ser Lys Pro Leu Asp Ser Ser Asp Glu Ser Leu Ile
305                 310                 315                 320

Asp Asp Glu Gly Tyr Lys Tyr Phe Ile Ala Ala Arg Lys Leu Ile Asp
                325                 330                 335

Ile Thr Asp Thr Arg Asp Thr Tyr Gly Ile Gln Thr Ile Val Met Leu
            340                 345                 350

Ile Ile Phe Leu Gln Cys Ser Ala Arg Leu Ser Thr Cys Tyr Ser Tyr
        355                 360                 365

-continued

Ile Gly Ile Ala Leu Arg Ala Ala Leu Arg Glu Gly Leu His Arg Gln
    370                 375                 380

Leu Asn Tyr Pro Phe Asn Pro Ile Glu Leu Glu Thr Arg Lys Arg Leu
385                 390                 395                 400

Phe Trp Thr Ile Tyr Lys Met Asp Ile Tyr Val Asn Thr Met Leu Gly
            405                 410                 415

Leu Pro Arg Thr Ile Ser Glu Glu Asp Phe Asp Gln Glu Met Pro Ile
        420                 425                 430

Glu Leu Asp Asp Glu Asn Ile Ser Glu Thr Gly Tyr Arg Phe Asp Leu
        435                 440                 445

Gln Gly Thr Lys Leu Ser Ser Ser Gly Ile Ala Asn Ala His Thr Arg
    450                 455                 460

Leu Ile Phe Ile Met Lys Lys Ile Val Lys Lys Leu Tyr Pro Val Lys
465                 470                 475                 480

Leu Gln Lys Pro Thr Ser Asn Ser Gly Asp Thr Pro Leu Glu Asn Asn
            485                 490                 495

Asp Leu Leu Ala His Glu Ile Val His Glu Leu Glu Met Asp Leu Gln
        500                 505                 510

Asn Trp Val Asn Ser Leu Pro Ala Glu Leu Lys Pro Gly Ile Glu Pro
    515                 520                 525

Pro Thr Glu Tyr Phe Lys Ala Asn Arg Leu Leu His Leu Ala Tyr Leu
530                 535                 540

His Val Lys Ile Ile Leu Tyr Arg Pro Phe Ile His Tyr Ile Ser Glu
545                 550                 555                 560

Lys Asp Lys Val Gly Asn Ser Ser Ile Pro Pro Ser Pro Glu Glu Ile
            565                 570                 575

Thr Ser Ile Glu Lys Ala Lys Asn Cys Val Asn Val Ala Arg Ile Val
        580                 585                 590

Val Lys Leu Ala Glu Asp Met Ile Asn Arg Lys Met Leu Ser Gly Ser
    595                 600                 605

Tyr Trp Phe Ser Ile Tyr Thr Ile Phe Phe Ser Val Ala Cys Leu Val
    610                 615                 620

Tyr Tyr Val His Phe Ala Pro Pro Lys Lys Asp Asn Gly Glu Leu Asp
625                 630                 635                 640

Pro Gln Tyr Met Glu Ile Lys Lys Asp Thr Glu Ser Gly Arg Glu Val
            645                 650                 655

Leu Asn Ile Leu Lys Asp Ser Ser Met Ala Ala Arg Arg Thr Tyr Asn
        660                 665                 670

Ile Leu Asn Ser Leu Phe Glu Gln Leu Asn Arg Arg Thr Ala Lys Val
    675                 680                 685

Asn Leu Ala Lys Ala Gln Gln Pro Pro Ser Gly Leu Asn Asn Pro Ala
    690                 695                 700

Ala Thr Gln Tyr Gln Lys Gln Gly Glu His Arg Gln Leu Gln Pro Ser
705                 710                 715                 720

Asn Tyr Ser Gly Thr Val Lys Ser Val Asp Pro Glu Asn Ile Asp Tyr
            725                 730                 735

Ser Ser Phe Gly Ser Gln Phe Glu Asn Thr Asn Ile Glu Asp Gly Ser
        740                 745                 750

Ser Asn Thr Lys Ile Asp Gln Lys Val Asn Gly Val Asn Tyr Ile Asp
    755                 760                 765

Gly Val Phe Thr Gly Ile Asn Leu Asn Met Pro Asn Leu Ser Glu Thr
    770                 775                 780

Ser Asn Thr Gln Gly Ile Asp Asn Pro Ala Phe Gln Ser Ile Asn Asn

```
                    785                 790                 795                 800
Ser Asn Leu Asn Asn Phe Val Gln Thr Lys Tyr Ile Pro Gly Met
            805                 810                 815
Met Asp Gln Leu Asp Met Lys Ile Phe Gly Arg Phe Leu Pro Pro Tyr
        820                 825                 830
Met Leu Asn Ser Asn Lys Val Glu Gln Gly Gln Asn Glu Arg Asn Leu
        835                 840                 845
Ser Gly Gln Pro Ser Ser Ser Asn Thr Pro Asp Gly Ser Gln Pro Val
    850                 855                 860
Thr Val Leu Asp Gly Leu Tyr Pro Leu Gln Asn Asp Asn Asn Asn
865                 870                 875                 880
His Asp Pro Gly Asn Ser Lys Ser Val Val Asn Asn Ser Asn Ser Val
                885                 890                 895
Glu Asn Leu Leu Gln Asn Phe Thr Met Val Pro Ser Gly Leu Ser Ser
            900                 905                 910
Thr Val Gln Asn Pro Glu Ala Ala Gln Lys Phe Asn Asn His Met Ser
        915                 920                 925
Asn Ile Ser Asn Met Asn Asp Pro Arg Arg Ala Ser Val Ala Thr Ser
        930                 935                 940
Asp Gly Ser Asn Asp Met Asp His His Ser Gln Gly Pro Ile Asn Lys
945                 950                 955                 960
Asp Leu Lys Pro Leu Ser Asn Tyr Glu Phe Asp Leu Phe Phe Asn
                965                 970                 975
Asp Trp Thr Thr Ala Pro Asp Thr Ile Asn Phe Asp Ser
            980                 985

<210> SEQ ID NO 2
<211> LENGTH: 2970
<212> TYPE: DNA
<213> ORGANISM: Pichia pastoris

<400> SEQUENCE: 2
atgcctccta acatcggct ggagcagagt atacagccca tggcttctca acaaatagta      60
cccggtaata aggttattct gccgaatcca aaagtagatg caaaatctac cccaaacatt    120
tcagttcaga agagaagaag agtcaccaga gcttgtgatg aatgtcggaa aagaaggtc     180
aaatgtgatg gtcaacaacc atgcattcat tgtaccgttt attcctatga gtgcacttac    240
agccaacctt ccagtaagaa gagacaggga caatctctga gtctgagtgc tccgtcaaac    300
attaatgcaa caagttccgt acaaaaatct gtaaaacctc tgaaatcga tttccaaagg     360
atgagagacg cactcaaata ttacgaagat cttttaaacc agttgatata ccccaacagt    420
gctccaactg ttcgagttaa tccgattcgt ctagcatcga tcttaaaaca attgagagcc    480
gataaatcaa gtgatgaatt aatttcagtc aaggctcttt ctgacaatta cattgagatg    540
cttcacaaaa cgatgcaaca acctgtacag cagccagctc ctccttcatt ggggcaagga    600
gggtccttct ctaatcacag tcccaatcat aataatgctt ctattgatgg ttccatagaa    660
tctaatctag ggagggaaat acgtatcata ttacctccga gagatattgc gctgaagctt    720
atctacaaga cttgggacaa cgcgtgtgta cttttccgct tttatcacag acccgcattt    780
attgaggacc tgaatgagtt atatgaaaca gatttggcaa actacaccaa taaacaacaa    840
aggttttac ctcttgtata ttcggtgatg gcttgtggtg ctcttttttg caagactgat     900
gggattaatc acggccaaaa gagctccaag cccaaagact cttctgatga agtctcata     960
gacgatgagg gttacaagta ttttattgcc gcaagaaaac taatagatat cacggatacc   1020
```

```
agggatacct acggaattca gactattgtt atgctgatca ttttttttaca atgttcggct   1080 cgtctttcaa catgctattc ttatattggc attgctctaa gagctgcatt gagagaaggt   1140
ttgcatcgtc agttgaacta tcctttcaat ccaattgagt tagaaacaag aaagcgtctt   1200
ttttggacta tctataaaat ggacatctat gtcaatacaa tgctgggggct tccaagaacc   1260 atttctgaag aggatttcga ccaggaaatg cctatcgaac ttgatgatga aacattagt   1320 gaaaccggat ataggttcga tttacaaggt acaaagttat ccagttcagg aatagccaat   1380
gctcacacta gattgatatt cataatgaag aaaattgtga aaaaattata tcctgtcaaa   1440
ctacagaaac caacctcaaa cagtggcgat accccacttg agaacaatga tttattggct   1500
catgaaatcg ttcatgaact tgagatggat ctccaaaatt gggtcaatag tctacctgca   1560 gaactaaaaac cggggataga accaccgacc gagtatttta aagctaacag attgcttcat   1620
ttggcatacc tgcatgtcaa gattattctc tacaggccat ttattcatta catctcagaa   1680
aaggataagg ttggaaatag ttctatccct ccgtcgcccg aagagatcac ttctatcgag   1740
aaagccaaga attgtgtcaa tgttgccaga attgttgtta aactagccga agacatgatt   1800
aataggaaaa tgttaagtgg ttcatattgg ttttccatttt ataccatttt tttttccgtg   1860
gcatgtctgg tgtactatgt tcatttcgct ccaccgaaga aagacaatgg agaactggat   1920
ccccaataca tggaaatcaa gaaagataca gagagtggaa gagaggtctt aaatatcctc   1980
aaagatagta gtatggcggc aagaagaacg tataatattc tcaactcttt gtttgagcag   2040
ttaaacagaa gaactgcaaa ggtcaaccta gcaaaggcac agcaaccacc atcagggttg   2100
aataacccag ctgctaccca gtatcagaaa cagggtgaac acaggcagtt acaaccaagt   2160
aactattctg gaactgtgaa atctgtggac ccagagaata tcgattactc ttcctttggt   2220
tctcagtttg aaaacactaa catcgaagat ggttcctcaa atacaaagat tgatcagaaa   2280
gtgaatgggg tgaactacat cgatggtgtg tttacaggga tcaacctaaa tatgcctaat   2340
ctctcagaaa cttctaacac tcaaggtatc gataatccag catttcaaag tataaacaat   2400
tctaatttga acaataattt tgtacaaaca aagtacattc ccggcatgat ggaccagcta   2460
gatatgaaaa ttttcggaag attccttcca ccttacatgc tgaactccaa caaggttgaa   2520
cagggacaaa atgaaaggaa cctatcaggc caaccatcct cgtcgaatac tcctgatgga   2580
tcacaacctg tgacagttct ggatggatta tacccgttgc agaatgataa taataataac   2640
cacgacccag gaaattcaaa gtctgttgta aataacagta actcggtaga aaacttacta   2700 cagaaccttta caatggtgcc ctcggggttg tcatcaacag tgcaaaatcc tgaagcggcc   2760
caaaaattca ataatcatat gtcaaacata tcgaatatga atgatccaag aagagctagc   2820
gtagctacat cagatggatc caatgacatg atcatcata gccaaggccc gataaacaaa   2880
gatttgaaac cgttgagcaa ctacgagttt gacgatctct tctttaatga ttggaccact   2940
gcgccagata caataaattt tgacagttaa                                    2970

<210> SEQ ID NO 3
<211> LENGTH: 640
<212> TYPE: DNA
<213> ORGANISM: Pichia pastoris

<400> SEQUENCE: 3
gcttaaggct gagagagaga gaggtatcac catcgacatc gctttgtgga agttcgagac    60
tccaaagtac cacgttaccg tcattgacgc tccaggtcac agagatttca ttaagaacat   120
gattaccggt acttcccaag ccgactgtgc cattttggtc attgcttccg gtattggtga   180
```

```
gttcgaggct ggtatctcca aggatggtca aaccagagag cacgctcttt tggctttcac      240
cctgggtgtc aagcaattga ttgttgccat caacaagatg gactccgtca atggtctca      300 aaagagatac gaggagattg tcaaggaaac ttccaacttc atcaagaagg ttggttacaa      360
ccctaagact gtcccattcg tcccaatttc cggatggaac ggtgacaaca tgattgagcc      420
atcttccaac tgtgactggt acaagggatg ggagaaggag accaaggctg gtggtgctac      480
caagggtaag accttgttgg aggctattga ctccattgac ccaccatcca gaccaactga      540
caagcctctg agattgcctt tgcaggatgt ctacaagatt ggtggtatcg aactgtgcc      600 agtcggtaga gttgagaccg gtgtcatcaa ggctggtatg                           640
```

<210> SEQ ID NO 4
<211> LENGTH: 213
<212> TYPE: PRT
<213> ORGANISM: Pichia pastoris

<400> SEQUENCE: 4

```
Leu Lys Ala Glu Arg Glu Arg Gly Ile Thr Ile Asp Ile Ala Leu Trp
1               5                   10                  15

Lys Phe Glu Thr Pro Lys Tyr His Val Thr Val Ile Asp Ala Pro Gly
            20                  25                  30

His Arg Asp Phe Ile Lys Asn Met Ile Thr Gly Thr Ser Gln Ala Asp
        35                  40                  45

Cys Ala Ile Leu Val Ile Ala Ser Gly Ile Gly Glu Phe Glu Ala Gly
    50                  55                  60

Ile Ser Lys Asp Gly Gln Thr Arg Glu His Ala Leu Leu Ala Phe Thr
65                  70                  75                  80

Leu Gly Val Lys Gln Leu Ile Val Ala Ile Asn Lys Met Asp Ser Val
                85                  90                  95

Lys Trp Ser Gln Lys Arg Tyr Glu Glu Ile Val Lys Glu Thr Ser Asn
            100                 105                 110

Phe Ile Lys Lys Val Gly Tyr Asn Pro Lys Thr Val Pro Phe Val Pro
        115                 120                 125

Ile Ser Gly Trp Asn Gly Asp Asn Met Ile Glu Pro Ser Ser Asn Cys
    130                 135                 140

Asp Trp Tyr Lys Gly Trp Glu Lys Glu Thr Lys Ala Gly Gly Ala Thr
145                 150                 155                 160

Lys Gly Lys Thr Leu Leu Glu Ala Ile Asp Ser Ile Asp Pro Pro Ser
                165                 170                 175

Arg Pro Thr Asp Lys Pro Leu Arg Leu Pro Leu Gln Asp Val Tyr Lys
            180                 185                 190

Ile Gly Gly Ile Gly Thr Val Pro Val Gly Arg Val Glu Thr Gly Val
        195                 200                 205

Ile Lys Ala Gly Met
    210
```

<210> SEQ ID NO 5
<211> LENGTH: 1467
<212> TYPE: DNA
<213> ORGANISM: Pichia pastoris

<400> SEQUENCE: 5

```
agtactagga ggatccagct catctaggga gtggaattga gtactgacac tcattactgg      60
aagaagtaga aagagtactg gttttgtggt agttccatat ttcagatgtc tgtagatggt     120
cgagcgaggt gaacatttca taggagattt cagaggagtt ggactttgaa atggtgaca     180
```

-continued

```
aaaggtagac agaagaaagg ttagagagtg tcagtgattc aaggtggttg cagagtacga      240
ccttgaacat tggtgggtat ttgacaggtt ggggagcaaa taagtgatga tgtcccatga      300
aagtagaaaa tggctagtag aaggcaaaaa tttgaaattc ttagagtcaa atagttagac      360
tccaagttct aatccacatt tggtcagttt catagcatcc agagcttttg ccactggtga      420
acatatctac ccattgcgat gcaacaagtc actgaaagcc taaaacggag attcccctat      480
cttacagcct cgttcaaaaa aactgctacc gtttatctgc tatggccgat gtgaggatgc      540
gctcatgccc aagagtccaa ctttatcaaa aacttgaccc gtcatacagg ctctagatca      600
agaagcaaac ttaatctcag catctggtta cgtaactctg caaccagta acacgcttaa      660 ggtttggaac aacactaaac taccttgcgg tactaccatt gacactacac atccttaatt      720
ccaatcctgt ctggcctcct tcaccttta accatcttgc ccattccaac tcgtgtcaga      780
ttgcgtatca agtgaaaaa aaaaaatttt aaatctttaa cccaatcagg taataactgt      840
cgcctctttt atctgccgca ctgcatgagg tgtcccctta gtgggaaaga gtactgagcc      900
aaccctggag gacagcaagg gaaaaatacc tacaacttgc ttcataatgg tcgtaaaaac      960
aatccttgtc ggatataagt gttgtagact gtcccttatc ctctgcgatg ttcttcctct     1020
caaagtttgc gatttctctc tatcagaatt gccatcaaga gactcaggac taatttcgca     1080
gtcccacacg cactcgtaca tgattggctg aaatttccct aaagaattc tttttcacga     1140 aaattttttt tttacacaag attttcagca gatataaaat ggagagcagg acctccgctg     1200
tgactcttct ttttttttctt ttattctcac tacatacatt ttagttattc gccaacatgg     1260
gtaaggaaaa gttgcacgtt aacgtcgttg ttattggaca cgtcgatgct ggtaaatcta     1320
ccaccaccgg tcacttgatc tacaagtgtg gtggtattga caagcgtacc atcgagaagt     1380
ttgaaaagga ggctgaagag ctcggtaagg gatctttcaa gtacgcctgg gttttggaca     1440
agcttaaggc tgagagagag agaggta                                          1467
```

<210> SEQ ID NO 6
<211> LENGTH: 17
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (12)..(12)
<223> OTHER INFORMATION: n is a, c, g, or t

<400> SEQUENCE: 6
ttyaartayg cntgggt       17

<210> SEQ ID NO 7
<211> LENGTH: 6
<212> TYPE: PRT
<213> ORGANISM: artificial
<220> FEATURE:
<223> OTHER INFORMATION: Primer ORF

<400> SEQUENCE: 7

Phe Lys Tyr Ala Trp Val
1               5

<210> SEQ ID NO 8
<211> LENGTH: 20
<212> TYPE: DNA
<213> ORGANISM: artificial
<220> FEATURE:
<223> OTHER INFORMATION: PCR primer

<400> SEQUENCE: 8
arytgytcrt grtgcatytc                                           20

<210> SEQ ID NO 9
<211> LENGTH: 7
<212> TYPE: PRT
<213> ORGANISM: artificial
<220> FEATURE:
<223> OTHER INFORMATION: Primer ORF

<400> SEQUENCE: 9

Glu Met His His Glu Gln Leu
1               5

<210> SEQ ID NO 10
<211> LENGTH: 20
<212> TYPE: DNA
<213> ORGANISM: artificial
<220> FEATURE:
<223> OTHER INFORMATION: PCR primer

<400> SEQUENCE: 10
tgacggtaac gtggtacttt                                           20

<210> SEQ ID NO 11
<211> LENGTH: 20
<212> TYPE: DNA
<213> ORGANISM: artificial
<220> FEATURE:
<223> OTHER INFORMATION: PCR primer

<400> SEQUENCE: 11
ggagtctcga acttccacaa                                           20

<210> SEQ ID NO 12
<211> LENGTH: 20
<212> TYPE: DNA
<213> ORGANISM: artificial
<220> FEATURE:
<223> OTHER INFORMATION: PCR primer

<400> SEQUENCE: 12
agcgatgtcg atggtgatac                                           20

<210> SEQ ID NO 13
<211> LENGTH: 41
<212> TYPE: DNA
<213> ORGANISM: artificial
<220> FEATURE:
<223> OTHER INFORMATION: PCR primer

<400> SEQUENCE: 13
tacagggcgc gtggggatat cggatccagc tcatctaggg a                   41

<210> SEQ ID NO 14
<211> LENGTH: 50
<212> TYPE: DNA
<213> ORGANISM: artificial
<220> FEATURE:
<223> OTHER INFORMATION: PCR primer

<400> SEQUENCE: 14
tgaagatgga tgggaatctc atatggttgg cgaataacta aatgtatgt            50

<210> SEQ ID NO 15

-continued

```
<211> LENGTH: 50
<212> TYPE: DNA
<213> ORGANISM: artificial
<220> FEATURE:
<223> OTHER INFORMATION: PCR primer

<400> SEQUENCE: 15
acatacattt tagttattcg ccaaccatat gagattccca tccatcttca        50

<210> SEQ ID NO 16
<211> LENGTH: 50
<212> TYPE: DNA
<213> ORGANISM: artificial
<220> FEATURE:
<223> OTHER INFORMATION: PCR primer

<400> SEQUENCE: 16
taattcgcgg ccgccctagg gaattcttac tcggtgacag cgcactcggg        50

<210> SEQ ID NO 17
<211> LENGTH: 40
<212> TYPE: DNA
<213> ORGANISM: artificial
<220> FEATURE:
<223> OTHER INFORMATION: PCR primer

<400> SEQUENCE: 17
ttttggtcat gcatgacgtc atagggagaa aaaccgagac                   40

<210> SEQ ID NO 18
<211> LENGTH: 29
<212> TYPE: DNA
<213> ORGANISM: artificial
<220> FEATURE:
<223> OTHER INFORMATION: PCR primer

<400> SEQUENCE: 18
ctcatatgtt ttgatgtttg atagtttga                               29

<210> SEQ ID NO 19
<211> LENGTH: 1055
<212> TYPE: DNA
<213> ORGANISM: Pichia pastoris

<400> SEQUENCE: 19
atagggagaa aaaccgagac aacgatggaa ctcccatgta gattccaccg ccccaattac    60
tgttttgggc aatcctgttg ataagacgca ttctagagtt gtttcatgaa agggttacgg   120
gtgttgattg gtttgagata tgccagagga cagatcaatc tgtggtttgc taaactggaa   180
gtctggtaag gactctagca agtccgttac tcaaaaagtc ataccaagta agattacgta   240
acacctgggc atgactttct aagttagcaa gtcaccaaga gggtcctatt taacgtttgg   300
cggtatctga acacaagac ttgcctatcc catagtacat catattaccct gtcaagctat   360
gctaccccac agaaatacccc caaaagttga agtgaaaaaa tgaaaattac tggtaacttc   420
acccccataac aaacttaata atttctgtag ccaatgaaag taaacccccat tcaatgttcc   480
gagatttagt atacttgccc ctataagaaa cgaaggattt cagcttcctt accccatgaa   540
cagaaatctt ccatttaccc cccactggag agatccgccc aaacgaacag ataatagaaa   600
aaagaaattc ggacaaatag aacactttct cagccaatta aagtcattcc atgcactccc   660
tttagctgcc gttccatccc tttgttgagc aacaccatcg ttagccagta cgaaagagga   720
aacttaaccg ataccttgga gaaatctaag gcgcgaatga gtttagccta gatatcctta   780
```

-continued

```
gtgaagggtt gttccgatac ttctccacat tcagtcatag atgggcagct ttgttatcat    840
gaagagacgg aaacgggcat taagggttaa ccgccaaatt atataaagac aacatgtccc    900
cagtttaaag tttttctttc ctattcttgt atcctgagtg accgttgtgt ttaatataac    960
aagttcgttt taacttaaga ccaaaaccag ttacaacaaa ttataacccc tctaaacact   1020
aaagttcact cttatcaaac tatcaaacat caaaa                              1055
```

<210> SEQ ID NO 20
<211> LENGTH: 32
<212> TYPE: DNA
<213> ORGANISM: artificial
<220> FEATURE:
<223> OTHER INFORMATION: PCR primer

<400> SEQUENCE: 20

```
actatttcga aatgcctcct aaacatcggc tg                                    32
```

<210> SEQ ID NO 21
<211> LENGTH: 25
<212> TYPE: DNA
<213> ORGANISM: artificial
<220> FEATURE:
<223> OTHER INFORMATION: PCR primer

<400> SEQUENCE: 21

```
gtcgacttaa ctgcaaaatt tattg                                            25
```

<210> SEQ ID NO 22
<211> LENGTH: 17
<212> TYPE: DNA
<213> ORGANISM: artificial
<220> FEATURE:
<223> OTHER INFORMATION: PCR primer

<400> SEQUENCE: 22

```
gatcctacgt agctgag                                                     17
```

<210> SEQ ID NO 23
<211> LENGTH: 17
<212> TYPE: DNA
<213> ORGANISM: artificial
<220> FEATURE:
<223> OTHER INFORMATION: PCR primer

<400> SEQUENCE: 23

```
aattctcagc tacgtag                                                     17
```

<210> SEQ ID NO 24
<211> LENGTH: 35
<212> TYPE: DNA
<213> ORGANISM: artificial
<220> FEATURE:
<223> OTHER INFORMATION: PCR primer

<400> SEQUENCE: 24

```
gatccaaacc atgagattcc catccatctt cactg                                 35
```

<210> SEQ ID NO 25
<211> LENGTH: 31
<212> TYPE: DNA
<213> ORGANISM: artificial
<220> FEATURE:
<223> OTHER INFORMATION: PCR primer

<400> SEQUENCE: 25

```
caaaccatga gattcccatc catcttcact g                                    31

<210> SEQ ID NO 26
<211> LENGTH: 37
<212> TYPE: DNA
<213> ORGANISM: artificial
<220> FEATURE:
<223> OTHER INFORMATION: PCR primer

<400> SEQUENCE: 26
cattctgttc ctctctcttt tccaaggaaa caccttc                              37

<210> SEQ ID NO 27
<211> LENGTH: 35
<212> TYPE: DNA
<213> ORGANISM: artificial
<220> FEATURE:
<223> OTHER INFORMATION: PCR primer

<400> SEQUENCE: 27
ggaaaagaga gaggaacaga atggaatgaa gttgg                                35

<210> SEQ ID NO 28
<211> LENGTH: 26
<212> TYPE: DNA
<213> ORGANISM: artificial
<220> FEATURE:
<223> OTHER INFORMATION: PCR primer

<400> SEQUENCE: 28
aattcttact cggtgacagc gcactc                                          26

<210> SEQ ID NO 29
<211> LENGTH: 22
<212> TYPE: DNA
<213> ORGANISM: artificial
<220> FEATURE:
<223> OTHER INFORMATION: PCR primer

<400> SEQUENCE: 29
cttactcggt gacagcgcac tc                                              22

<210> SEQ ID NO 30
<211> LENGTH: 1236
<212> TYPE: DNA
<213> ORGANISM: artificial
<220> FEATURE:
<223> OTHER INFORMATION: Citrobacter braakii phytase codon optimized for
      expression in P.pastoris

<400> SEQUENCE: 30
gaggaacaga atggaatgaa gttggagaga gttgtcatcg tttctagaca cggtgttaga     60
gctcccacca aattcactcc aatcatgaag aacgtcaccc cagatcagtg gccacaatgg    120
gacgtcccac tgggctggtt gactccacgt ggtggagaac ttgtctctga attgggtcag    180
taccagagac tgtggttcac ctccaaagga cttctgaata accaaacttg cccatcccca    240
ggacaagtcg ctgttattgc cgacaccgat caaagaacca gaaaaaccgg agaggccttt    300
ttggcaggac ttgctccaaa atgccagatt caagtccact accaaaaaga cgaagagaag    360
aacgatccat tgttcaatcc cgtcaagatg ggaaaatgct cctttaacac cttgcaagtc    420
aaaaacgcca ttttggaaag agcaggtggc aatatcgagc tttacaccca gcgttaccaa    480 tcttcttttta gaactttgga aaatgttttg aactttagtc agtccgagac ttgcaagacc    540
accgagaagt ctaccaagtg cactttgccc gaggctttgc cctccgagct aaggtcact    600
```

```
cccgataacg tctccttgcc aggagcatgg tctctttcct ccactttgac cgagattttc    660
ttgttgcagg aggcacaagg aatgccacag gtcgcatggg gtagaattac cggtgaaaag    720
gaatggagag acttgctgtc tcttcacaac gcccagttcg atctcttgca gagaacccca    780
gaggttgcca gatccagagc tactccactt ttggatatga tcgacaccgc tttgctgacc    840
aatggtacca ccgagaacag atacggtatt aagttgccag tctccttgct gttcattgca    900
ggtcacgaca ccaatttggc caacttgtct ggagccttgg acctgaactg gtctttgcca    960
ggacagcccg acaataccccc accaggaggc gaattggttt cgaaaagtg aaaagaacc   1020 tccgataaca ccgattgggt ccaagtctcc ttcgtctacc aaaccttgag agatatgcgt   1080
gacattcagc cactgtcttt ggagaagccc gctggtaagg ttgacttgaa attgatcgct   1140
tgcgaagaaa agaactccca gggaatgtgc tctttgaagt ccttttccag attgatcaag   1200
gagattagag tccccgagtg cgctgtcacc gagtaa                             1236

<210> SEQ ID NO 31
<211> LENGTH: 255
<212> TYPE: DNA
<213> ORGANISM: artificial
<220> FEATURE:
<223> OTHER INFORMATION: S. cerevisiae alpha factor signal codon
      optimized for expression in P. pastoris

<400> SEQUENCE: 31
atgagattcc catccatctt cactgctgtt tgttcgctg cttcctccgc tttggctgct    60
ccagttaaca ctactactga agatgaaact gctcaaatcc cagctgaagc tgttatcggt   120
tactccgact ggaaggtga tttcgacgtt gctgttttgc cattctccaa ctccaccaac   180
aacggattgt tgttcattaa caccaccatt gcttccatcg ctgctaagga agaaggtgtt   240
tccttggaaa agaga                                                    255

<210> SEQ ID NO 32
<211> LENGTH: 31
<212> TYPE: DNA
<213> ORGANISM: Artificial
<220> FEATURE:
<223> OTHER INFORMATION: PCR primer

<400> SEQUENCE: 32
gcgcgaattc cacagggctt gctaagaaat c                                  31

<210> SEQ ID NO 33
<211> LENGTH: 21
<212> TYPE: DNA
<213> ORGANISM: Artificial
<220> FEATURE:
<223> OTHER INFORMATION: PCR primer

<400> SEQUENCE: 33
gaagggagat taatacaggg c                                             21

<210> SEQ ID NO 34
<211> LENGTH: 23
<212> TYPE: DNA
<213> ORGANISM: Artificial
<220> FEATURE:
<223> OTHER INFORMATION: PCR primer

<400> SEQUENCE: 34
gattggacca ctgcgccaga tac                                           23
```

```
<210> SEQ ID NO 35
<211> LENGTH: 29
<212> TYPE: DNA
<213> ORGANISM: Artificial
<220> FEATURE:
<223> OTHER INFORMATION: PCR primer

<400> SEQUENCE: 35
gcgcgtcgac ccacccgagg ataagaagg                                    29

<210> SEQ ID NO 36
<211> LENGTH: 42
<212> TYPE: DNA
<213> ORGANISM: Artificial
<220> FEATURE:
<223> OTHER INFORMATION: PCR primer

<400> SEQUENCE: 36
ccctgtatta atctcccttc atcagaattg gttaattggt tg                     42

<210> SEQ ID NO 37
<211> LENGTH: 40
<212> TYPE: DNA
<213> ORGANISM: Artificial
<220> FEATURE:
<223> OTHER INFORMATION: PCR primer

<400> SEQUENCE: 37
tctggcgcag tggtccaatc atcgataagc tttaatgcgg                        40

<210> SEQ ID NO 38
<211> LENGTH: 20
<212> TYPE: DNA
<213> ORGANISM: Artificial
<220> FEATURE:
<223> OTHER INFORMATION: PCR primer

<400> SEQUENCE: 38
ctggagcaga gtatacagcc                                              20

<210> SEQ ID NO 39
<211> LENGTH: 21
<212> TYPE: DNA
<213> ORGANISM: Artificial
<220> FEATURE:
<223> OTHER INFORMATION: PCR primer

<400> SEQUENCE: 39
ctcaataaat gcgggtctgt g                                            21

<210> SEQ ID NO 40
<211> LENGTH: 20
<212> TYPE: DNA
<213> ORGANISM: Artificial
<220> FEATURE:
<223> OTHER INFORMATION: PCR primer

<400> SEQUENCE: 40
cctggttgat cagctccacc                                              20

<210> SEQ ID NO 41
<211> LENGTH: 21
<212> TYPE: DNA
<213> ORGANISM: Artificial
<220> FEATURE:
<223> OTHER INFORMATION: PCR primer
```

<400> SEQUENCE: 41
cccgtcaagt cagcgtaatg c                                           21

<210> SEQ ID NO 42
<211> LENGTH: 20
<212> TYPE: DNA
<213> ORGANISM: Artificial
<220> FEATURE:
<223> OTHER INFORMATION: PCR primer

<400> SEQUENCE: 42
ctccctctcc agctgcttcg                                             20

<210> SEQ ID NO 43
<211> LENGTH: 20
<212> TYPE: DNA
<213> ORGANISM: Artificial
<220> FEATURE:
<223> OTHER INFORMATION: PCR primer

<400> SEQUENCE: 43
cggtgcctga ctgcgttagc                                             20

<210> SEQ ID NO 44
<211> LENGTH: 50
<212> TYPE: DNA
<213> ORGANISM: Artificial
<220> FEATURE:
<223> OTHER INFORMATION: PCR primer

<400> SEQUENCE: 44
ataaattttg acagttaagt cgacctctgt aaattaattg ataatttcaa             50

<210> SEQ ID NO 45
<211> LENGTH: 60
<212> TYPE: DNA
<213> ORGANISM: Artificial
<220> FEATURE:
<223> OTHER INFORMATION: PCR primer

<400> SEQUENCE: 45
caatgatgat gatgatgatg gtcgacgttt aaacttaatt aaaagggaaa tttacaagcc   60

<210> SEQ ID NO 46
<211> LENGTH: 39
<212> TYPE: DNA
<213> ORGANISM: artificial
<220> FEATURE:
<223> OTHER INFORMATION: PCR primer

<400> SEQUENCE: 46
attgaacaac tatttcgaaa ccatgagcaa tctaccccc                        39

<210> SEQ ID NO 47
<211> LENGTH: 37
<212> TYPE: DNA
<213> ORGANISM: artificial
<220> FEATURE:
<223> OTHER INFORMATION: PCR primer

<400> SEQUENCE: 47
gagtttttgt tctagaatga caccaccatc tagtcgg                          37

<210> SEQ ID NO 48
<211> LENGTH: 12
<212> TYPE: PRT

-continued

```
<213> ORGANISM: artificial
<220> FEATURE:
<223> OTHER INFORMATION: alignment example sequence

<400> SEQUENCE: 48

Ala Cys Met Ser His Thr Trp Gly Glu Arg Asn Leu
1               5                   10

<210> SEQ ID NO 49
<211> LENGTH: 14
<212> TYPE: PRT
<213> ORGANISM: artificial
<220> FEATURE:
<223> OTHER INFORMATION: aligment example sequence

<400> SEQUENCE: 49

His Gly Trp Gly Glu Asp Ala Asn Leu Ala Met Asn Pro Ser
1               5                   10

<210> SEQ ID NO 50
<211> LENGTH: 8
<212> TYPE: PRT
<213> ORGANISM: Artificial Sequence
<220> FEATURE:
<223> OTHER INFORMATION: alignment example sequence

<400> SEQUENCE: 50

His Thr Trp Gly Glu Arg Asn Leu
1               5

<210> SEQ ID NO 51
<211> LENGTH: 9
<212> TYPE: PRT
<213> ORGANISM: Artificial Sequence
<220> FEATURE:
<223> OTHER INFORMATION: alignment example sequence

<400> SEQUENCE: 51

His Gly Trp Gly Glu Asp Ala Asn Leu
1               5
```